United States Patent [19]

McGregor

[11] 4,371,465
[45] Feb. 1, 1983

[54] MAMMALIAN COLLAGENASE INHIBITORS

[75] Inventor: William H. McGregor, Malvern, Pa.

[73] Assignee: American Home Products Corporation, New York, N.Y.

[21] Appl. No.: 309,367

[22] Filed: Oct. 7, 1981

[51] Int. Cl.³ .................... C07C 103/52; A61K 37/00
[52] U.S. Cl. ............................. 260/112.5 R; 424/177
[58] Field of Search .................. 424/177; 260/112.5 R

[56] References Cited

U.S. PATENT DOCUMENTS 4,235,885 11/1980 Sundoon et al. .................... 424/177
4,276,284 6/1981 Brown .................................. 424/177

OTHER PUBLICATIONS

Ajinomoto KK, "Japanese Patent Abstract," 3028-165, 8-30-76.
Harper, Ann. Rev. Biochem., 1980, 49: 1063-1078.

Primary Examiner—Delbert R. Phillips
Assistant Examiner—F. T. Moezie
Attorney, Agent, or Firm—Richard K. Jackson

[57] ABSTRACT

The polypeptides

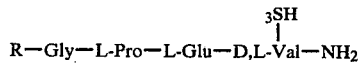

in which R is hydrogen, alkanoyl of 2 to 6 carbon atoms, cycloalkylcarbonyl of 2 to 6 carbon atoms or a pharmaceutically acceptable salt thereof act as collagenase inhibitors useful in the treatment of diseases involving excessive tissue destruction by collagenase.

2 Claims, No Drawings

MAMMALIAN COLLAGENASE INHIBITORS

BACKGROUND OF THE INVENTION

Approximately thirty percent of the body protein of mammals is comprised of collagen, a long rod-like polypeptide containing three parallel chains of coiled-coil structure with a molecular weight of about 300,000. Collagen existing in skin, cartilage, bone and tendon is composed of two α1 chains and one α2 chain of roughly one thousand amino acids each. The α1 sequence is completely known and substantial sequences of the α2 chain have been elucidated.

Collagenase effects an ultra-specific cleavage of collagen at a site one quarter the length of the molecule from the C-terminus.

Collagenase is produced by rheumatoid synovial cells at a rate higher than it is produced by normal cells and the destructive events of rheumatoid arthritis can be correlated with the generation of collagenase. Collagenase has also been found to be involved in disease states resulting in tissue destruction of the stomach, eye, middle ear, peridontal membranes and skin. The administration of a collagenase inhibitor to prevent tissue destruction is an indicated method of treatment for disease states involving proteolytic destruction of collagen.

Collagenase is a metallo enzyme of molecular weight about 40,000 with a requirement of zinc. The enzyme is known to be inhibited by chelating agents such as ethylenediaminetetraacetic acid, o-phenanthroline, penicillamine and disulfide reducing agents such as cysteine and dithiothreitol as well as a number of poorly characterized naturally occurring substances.

DESCRIPTION OF THE INVENTION

In accordance with this invention there is provided a group of polypeptides which inhibit the activity of the enzyme collagenase. The polypeptides of this invention present the structural formula:

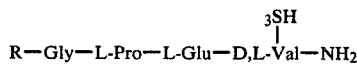

in which
R is hydrogen, alkanoyl of 2 to 6 carbon atoms, cycloaklylcarbonyl of 6 to 8 carbon atoms or alkoxycarbonyl of 2 to 6 carbon atoms;
or a pharmaceutically acceptable salt thereof.

The pharmaceutically acceptable salts of the polypeptides of this invention include salts derived from either organic or inorganic acids such as acetic, lactic, succinic, benzoic, salicylic, methanesulfonic, toluenesulfonic, hydrochloric, sulfuric or phosphoric acid, and the like. Desired salts may be produced from other salts via conventional treatment with ion exchange resins. The N-terminal acyl groups depicted as R in the structural formula, supra, are preferably alkanoyl or cycloalkanoyl moieties as defined and more preferably either the acetyl or cyclopentylcarbonyl groups.

The compounds of this invention are produced by conventional solution phase techniques or solid phase techniques employing a benzhydrylamine polystyrene resin support. Thus, the individual amino acids or preformed di- or tri-peptides necessary for the formation of the desired polypeptide or their activated derivatives are condensed with formation of carbamide (—CONH—) bondings in the desired order of succession while temporarily protecting any reactive group which could undesirably enter into the condensation reaction. In the case of 3-mercapto valine, the side chain mercapto protecting group may be acetamidomethyl, trityl, carbamoyl, thioethyl, thiotertiarybutyl or preferably p-methoxybenzyl. The applicable α-amino protecting groups are those well known to the art or preferably tert-butyloxycarbonyl.

The inhibitory effect of the compounds of this invention toward collagenase was determined following the procedure of Sellers et al., Biochem J. 167 353–360 (1977) whereby the 2mM of the inhibitor being tested is incubated at 35° C. for from 5 to 18 hours (depending upon the potency of the collagenase) with collagen and collagenase (buffered with Tris ®-CaCl$_2$; pH 7.4). The collagen is acetyl $^{14}$C collagen. The samples are centrifuged and an aliquot removed for assay on a scintillation counter. Because native collagen forms insoluble fibrils under the test conditions, the supernatant liquid contains radioactivity as a measure of hydrolysis. The collagenase activity in the presence of 2mM inhibitor is compared to activity in a control devoid of inhibitor and the results reported as percent inhibition of collagenase activity. Each of the compounds of this invention have been established as active collagenase inhibitors by the test procedure.

Thus, the compounds of this invention are useful in the treatment of disease states involving excessive collagen destruction by collagenase such as rheumatoid arthritis and diseases evidenced by tissue destruction of the stomach, eye, middle ear, peridontal membranes, skin. The dosage of the collagenase inhibitors of this invention will vary with the mode of administration (oral, parenteral, topical, intramuscular, etc.) and the condition of the specific patient under treatment. Proper dosing may be readily established by initial administration of small amounts o the inhibitor, ca. 100 μg/kg. followed by increased doses until the optimum effect is achieved in a specific human or non-human mammalian patient. When sustained release treatment is desired, the polypeptides may be placed in conventional depot dosage forms such as a Silastic ® capsule or slow release pellet formulations conventional to the art.

The following example illustrates the preparation of a typical, representative compound of the invention. The precent inhibition of collagenase activity at the 2 mM polypeptide level in accordance with the previously described standard testing procedure is provided after the preparatory description is compared to D-penicillamine alone, the latter being a known collagenase inhibitor.

EXAMPLE

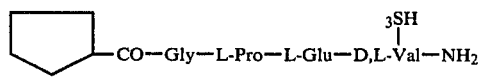

7.5 Grams of benzhydrylamine . HCl resin were washed with 30% TEA in MeCl$_2$ (2 times), MeCl$_2$ (1 x), DMF (2 x) and coupled with 10 gm t-Boc-DL-p-methoxybenzyl penicillamine, 4 gm hydroxybenzotriazole (HOBT) and 4 ml diisopropylcarbodiimide (DIC) overnight. The aminoacyl resin was trace ninhydrin positive after successive washing with DMF (1 x), MeCl$_2$ (2 x), MeOH and MeCl$_2$ and was recoupled with 5 gm t-Boc-DL-p-methoxybenzyl-penicillamine, 2 gm HOBT and 2 ml DIC overnight. After the usual washing at this step, it was ninhydrin negative, was deprotected with 50% trifluoroacetic acid (TFA) in MeCl₂ as usual for this step, washed in the previously described manner for this stage and coupled with 7.5 gm t-Boc-L-glutamine, 4 gm HOBT and 4 ml DIC over the weekend. After the usual washing at this stage the peptidyl-resin was ninhydrin negative, was deprotected with TFA in the predescribed fashion washed as described previously for this step and coupled with 7 gm t-Boc-L-proline, 4 gm HOBT and 4 ml DIC as usual. The resin was recoupled twice in the usual fashion with the above quantities of reagent before it was ninhydrin negative. After washing the peptido resin was deprotected with TFA in the usual way for this stage and coupled with 6 gm t-Boc glycine, 4 gm HOBT and 4 ml DIC over 72 hours. After washing, it was recoupled as usual, with similar amounts of t-Box-glycine, HOBT and DIC and washed as usual, at which point it was ninhydrin negative, deprotected as usual with TFA and coupled with 5 grams cyclopentane carboxylic acid, 4 gm HOBT and 4 ml DIC overnight as usual. The peptidyl-resin was ninhydrin negative after the usual washing at this stage, and was dried in vacuo.

The above peptidyl-resin was cleaved and deprotected with HF in the presence of 10 ml of anisole for 1 hr at 0° C. and the HF removed in vacuo. The residue was triturated 3 times with Et₂O dried in a stream of nitrogen, triturated with 150 ml 0.2 N HOAc and lyophylized 944 mg of crude peptide.

150 mg. of the crude peptide were purified on a column of Sephadex G-10 using 0.2 N HOAc at a flow rate of 15 ml/hr and collecting 1 ml fractions. Fractions 64–72 were combined on the basis of TLC (S. G. BAW peptide-chlorine spray) and lyophylized, 63 mg.

Amino Acid Ratios: Gly 1.0, Pro 1.02, Glu 0.96, NH₃ 2.2 Penicillamine appeared but is not quantitated.

Percent inhibition collagenase: 86

Percent inhibition collagenase by D-penicillamine=39.

What is claimed is:

1. A compound of the formula:

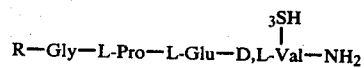

in which
R is hydrogen, alkanoyl of 2 to 6 carbon atoms, cycloalkylcarbonyl of 6 to 8 carbon atoms or alkoxycarbonyl of 2 to 6 carbon atoms;
or a pharmaceutically acceptable salt thereof.

2. The compound of claim 1 which is

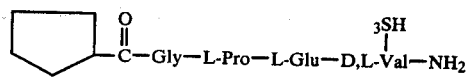

or a pharmaceutically acceptable salt thereof.

* * * * *